(12) United States Patent
Lo et al.

(10) Patent No.: US 8,180,574 B2
(45) Date of Patent: May 15, 2012

(54) SIMPLIFIED PERITONEAL EQUILIBRATION TEST FOR PERITONEAL DIALYSIS

(75) Inventors: Ying-Cheng Lo, Green Oaks, IL (US); Alp Akonur, Evanston, IL (US); Sarah Stobo Prichard, Highland Park, IL (US)

(73) Assignees: Baxter International, Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 349 days.

(21) Appl. No.: 12/498,847

(22) Filed: Jul. 7, 2009

(65) Prior Publication Data
US 2011/0010101 A1    Jan. 13, 2011

(51) Int. Cl.
G01N 33/48 (2006.01)
G06F 19/00 (2011.01)

(52) U.S. Cl. ............. 702/19; 702/30; 702/179; 702/180

(58) Field of Classification Search .................... 702/19, 702/22, 30–32, 121–123, 179–181; 604/28
See application file for complete search history.

(56) References Cited

U.S. PATENT DOCUMENTS

| | | | |
|---|---|---|---|
| 4,192,748 A | 3/1980 | Hyden | |
| 4,244,787 A | 1/1981 | Klein et al. | |
| 4,508,622 A | 4/1985 | Polaschegg et al. | |
| 5,141,327 A | 8/1992 | Shiobara | |
| 5,360,013 A | 11/1994 | Gilbert | |
| 5,442,969 A | 8/1995 | Troutner et al. | |
| 5,518,623 A | 5/1996 | Keshaviah et al. | |
| 5,567,320 A | 10/1996 | Goux et al. | |
| 5,725,773 A | 3/1998 | Polaschegg | |
| 5,733,442 A | 3/1998 | Shukla | |
| 5,744,031 A | 4/1998 | Bene | |
| 5,788,846 A | 8/1998 | Sternby | |
| 5,954,951 A | 9/1999 | Nuccio | |
| 5,989,423 A * | 11/1999 | Kamen et al. | 210/258 |
| 6,247,840 B1 | 6/2001 | Gaffar | |
| 7,115,113 B2 | 10/2006 | Evans et al. | |

(Continued)

FOREIGN PATENT DOCUMENTS
EP    0 621 046    10/1994
(Continued)

OTHER PUBLICATIONS

International Search Report and Written Opinion for International Application No. PCT/US2010/037082 mailed on Aug. 31, 2010.

(Continued)

*Primary Examiner* — Phuong Huynh
(74) *Attorney, Agent, or Firm* — K&L Gates LLP

(57) ABSTRACT

A simplified peritoneal equilibration test (S-PET) is disclosed. Instead of a lengthy peritoneal equilibration test (PET), the simplified procedure requires no blood sample and may use data from as few as two or three samples to classify a peritoneal membrane of a user. Typically, a peritoneal membrane or peritoneum of a dialysis patient, or other person, is classed as a high transport membrane, high-average transport membrane, a low-average transport membrane or a low transporter membrane. The S-PET may be performed at home by a user without the need to submit a blood sample. Kits for analyzing the samples may be furnished for home use. The kits may use disposable strips, microfluidic analyzers or chemical reagents, or may alternatively include reusable analysis equipment, such as optical or conductivity analysis equipment.

23 Claims, 5 Drawing Sheets

U.S. PATENT DOCUMENTS

| | | | |
|---|---|---|---|
| 7,303,541 B2 | 12/2007 | Hamada et al. | |
| 2005/0089994 A1* | 4/2005 | Neftel | 435/287.1 |
| 2007/0112297 A1 | 5/2007 | Plahey et al. | |

FOREIGN PATENT DOCUMENTS

| | | |
|---|---|---|
| EP | 0 711 569 | 5/1996 |
| EP | 1535576 * | 1/2005 |
| EP | 1 535 576 | 6/2005 |
| FR | 2 696 644 | 4/1994 |
| JP | 2000 271127 | 10/2000 |
| WO | 82/04127 | 11/1982 |
| WO | 03/063929 | 8/2003 |

OTHER PUBLICATIONS

Vonesh E. F., Story K, O'Neill WT for The PD ADEQUEST International Study Group. Perit Dial Int 1999; 19:556-571.

Heimburger O, Waniewski J. Ultrafiltration Failure in Peritoneal Dialysis Patients. Perit Dial Int 2004; 24:506-508.

Mujais S, Nolph K, Gokal R, et al. Evaluation and Management of Ultrafiltration Problems in Peritoneal Dialysis. Perit Dial Int 2000; 20:S4, S5-21.

Abu-Alfa Ak, Burkhard J, Piraino b, Pulliam J, Mujais S. Approach to Fluid Management in Peritoneal Dialysis: A Practical Algorithm. Kidney Int 2002; 62:S81 S8-S16.

La Milia V, Di Filippo, Crepaldi M et al. Mini-Peritoneal Equilibration Test: A Simple and Fast Method to Assess Free Water and Small Solute Transport Across the Peritoneal Membrane. Kidney Int 2005; 68:840-846.

Blake P. Individualized Prescription of Peritoneal Dialysis Therapy. Peritoneal Dialysis International, vol. 19, Supp. 2, 1999.

Brunkhorst R. Individualized PD Prescription: APD Versus CAPD. Peritoneal Dialysis International, vol. 25, Supp. 3, 2005.

Rippe B. et al. Computer Simulation of Peritoneal Fluid Transport in CAPD. Kidney International, vol. 40 (1991), pp. 315-325.

Waniewski J. Mathematical Modeling of Fluid and Solute Transport in Hemodialysis and Peritoneal Dialysis. J. of Membrane Science 274 (2006), 24-37.

Vonesh E. et al. Kinetic Modeling as a Prescription Aid in Peritoneal Dialysis. Blood Purif 1991; 9: 246-270.

Prowant BF, Schmidt LM. The Peritoneal Equilibration Test: A Nursing Discussion. *Anna J.* 1991; 18:361-366.

Schmidt LM, Prowant BF. How to do a Peritoneal Equilibration Test. *Anna J.* 1991; 18: 368-370.

Twardowski ZJ, Nolph KD, Khanna R, et al. Peritoneal Equilibration Test. *Perit Dial Bull.* 1987; 7:138-147.

Twardowski ZJ, Clinical Value of Standardized Equilibration Tests in CAPD patients. *Blood Purif.* 1989; 7:95-108.

Twardowski ZJ, Prowant BF, Moore HL, Lou LC, White E, Farris K. Short Peritoneal Equilibration Test: Impact of Preceding Dwell Time. *Adv Perit Dial.* 2003: 19:53-58.

Lilaj T, Dittrich E, Puttinger H, et al. A Preceding Exchange with Polyglucose Versus Glucose Solution Modifies Peritoneal Equilibration Test Results. *Am J Kidney Dis*. 2001; 38:118-126.

Adcockl A., Fox K., Walker P., and Raymond K., Clinical Experience and Comparative Analysis of the Standard and Fast Peritoneal Equilibration Tests (PET), Advances in PD, vol. 8: 59-61, 1992.

Pannekeet et al., The standard peritoneal permeability analysis: A tool for the assessment of peritoneal permeability characteristics in CAPD patients, Kidney Int. 1995; 48:866-875.

Vonesh E. F. and Rippe B., Net fluid absorption under membrane transport models of peritoneal dialysis, Blood Purif 1992; 10:209-226.

Passadakis P. and Oreopoulos D. G., Peritoneal Dialysis in Patients with Acute Renal Failure, Advances in Peritoneal Dialysis, vol. 23, 7-16, 2007.

Akonur, et al. Ultrafiltration Efficiency During Automated Peritoneal Dialysis Using Glucose-Based Solutions, Advances in Peritoneal Dialysis, vol. 24, 69-74, 2008.

La Milia et al. Simultaneous measurement of peritoneal glucose and free water osmotic conductances, Kidney International vol. 72, 643-650, 2007.

Agrawal and Nolph Advantages of A Tidal Peritoneal Dialysis, Peritoneal Dialysis International, vol. 20, S98-S100, 2000.

International Preliminary Report on Patentability for International Application No. PCT/US2010/037082 mailed on Dec. 7, 2010.

* cited by examiner

SIMPLIFIED PERITONEAL EQUILIBRATION TEST FOR PERITONEAL DIALYSIS

RELATED APPLICATION

The present application is related to U.S. application Ser. No. 12/498,853, Peritoneal Dialysis Therapy with Large Dialysis Solution Volumes, which was filed concurrently with the present application.

BACKGROUND

The present disclosure relates generally to medical fluid delivery systems and methods. More particularly, this disclosure includes systems, methods and apparatuses for administering a simplified peritoneal equilibration test. The test will more easily help the patient and caregivers to determine whether a patient will benefit from peritoneal dialysis. The test is also useful for helping to determine particular optimal therapies that may be administered to the patient.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

Peritoneal dialysis machines are used to accomplish this task. Such machines are described, for example, in the following U.S. patents, all of which are incorporated by reference in their entirety, as though each patent were set forth herein, page by page, in its entirety: U.S. Pat. Nos. 5,350,357; 5,324,422; 5,421,823; 5,431,626; 5,438,510; 5,474,683; 5,628,908; 5,634,896; 5,938,634; 5,989,423; 7,153,286; and 7,208,092.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement. In particular there is room for improvement in the selection of dwell times for the patient.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. These systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes and other neutral solutes) moves across a membrane, such as a dialyzer or peritoneal membrane. For example, ultrafiltration in peritoneal dialysis is a result of osmotic and hydrostatic pressure differences between blood and dialysate across the patient's peritoneal membrane. It is also important to control the concentration of metabolic substances in the patient's bloodstream, such as urea concentration, $\beta_2$-microglobulin, creatinine concentration, and so forth. Each of these, along with many other variables, constitutes a peritoneal dialysis outcome.

Each patient is different, possessing for instance, a unique peritoneal membrane, its own separation characteristics, and its unique response to peritoneal dialysis. Each patient is also different with respect to body surface area (BSA) and total body water volume, which also have an effect on transport characteristics. Each patient is different in terms of transport characteristics that relate to the ultrafiltration rate. Each patient is also different in terms of response to dialysis, that is, the amount of water and waste removed in a given time period, using a given fill volume, a particular dialysis fluid, and so forth.

One basic difference among patients is the rate at which water and metabolic wastes pass from the patient's bloodstream through the peritoneal membrane. Once the water and wastes pass through the peritoneal membrane, they are absorbed into the dialysis therapy fluid that has been placed into the patient's peritoneal cavity, and then removed from the patient. A peritoneal equilibration test (PET) determines the relative rate of transmembrane transport. Patients can then be classified as high-rate transporters, high-average transporters, low-average transporters, or low-rate transporters, depending on the speed of waste removal and the speed of absorption of glucose from the dialysis fluid. Other peritoneal membrane transport categories or classes may also be used, such as high, average, and low transporters. Patients may also be classified in terms of their total body surface area (BSA), which depends only on the patient's height and weight.

In general, the rate of water removal is different from the rate of waste removal, and both depend on the patient transporter type and is indirectly related to the patient membrane transport type. For example, fast transporters can quickly pass metabolic waste, but glucose from the dialysis solution is rapidly absorbed into the body. As a result, glucose concentration in the dialysate decreases and the osmotic gradient or driving force diminishes within a variable period of time, depending on the patient transporter type. For instance, high transporters may benefit more from short dwell times, such as those used in automated peritoneal dialysis (APD), where the effect of high osmotic gradients is still present.

Conversely, the osmotic gradient will be sustained for a longer period of time in the case of a low transporter patient, resulting in a larger volume of ultrafiltrate removal. Such a patient will likely benefit from a longer dwell time, such as a continuous ambulatory peritoneal dialysis (CAPD) and with perhaps only a single nighttime exchange. Much useful information about a patient's response to therapy can be learned from administering the PET to the patient. The results of the PET can then be used to administer the therapy that would lead to the best outcome for that patient.

However, present PET tests also require a blood test. A test that requires at least one blood sample for confirmation of the level of certain waste products in the patient's blood, such as creatinine, also requires time for a technician to calculate the ratio of the concentration of the substance in the dialysate to the concentration of the substance in the blood plasma. Thus, while the PET can be valuable in deciding the general characteristics of a patient, the difficulty in administering the PET may be a significant barrier in determining the therapy best suited for a patient. This is because the present PET requires the patient to visit a dialysis center, requires a nurse's time as well as the patient's time to obtain a blood sample, and causes discomfort to the patient. The costs associated with the test must also be borne by the patient, his insurance carrier, or the ultimate payor. What is needed is a better way to decide a patient's response to dialysis, a more convenient test such that the treatment will yield an appropriate therapy outcome for that patient, but will be more cost-effective and less invasive for the patient.

SUMMARY

One embodiment of the present disclosure is system for performing a simplified peritoneal equilibration test ("S-PET"). The system includes a computer and a software program on a computer-readable medium accessible to the computer, wherein the software program is programmed to accept inputs concerning at least two concentrations of a substance in samples of a dialysis fluid only from at least two separate times after a start of a dialysis therapy of a patient, wherein the software program includes a formula $(CD_t - CD_{eq}) = (CD_0 - CD_{eq})e^{-(t/\tau)}$, where $CD_t$ is a concentration of the substance in the dialysis fluid at time t, $CD_{eq}$ is an equilibrium concentration of the substance, $CD_0$ is an initial concentration of the substance in the dialysis fluid, t is time and $\tau$ is an equilibration time constant of a transport property of a peritoneum of the patient for the substance. In this embodiment, the software program is programmed to use the formula to calculate the equilibrium concentration of the substance, wherein the equilibrium concentration of the substance in the dialysis fluid is approximately equal to an equilibrium concentration of the substance in the patient's blood. The software is further programmed to suggest at least one transport property of the peritoneum of the patient. In another embodiment, the software is programmed to suggest whether the peritoneum of the patient has a transport property selected from the group consisting of: a high transporter property, a high-average transporter property, a low-average transporter property, and a low transporter property.

Another embodiment of the present disclosure is a system for performing a simplified peritoneal equilibration test. The system includes a peritoneal dialysis machine, a computer for operating the peritoneal dialysis machine, and a software program on a computer-readable medium accessible to the computer, wherein the software program is programmed to accept inputs concerning at least two concentrations of a substance in samples of a dialysis fluid only from at least two separate times after a start of a dialysis therapy of a patient, wherein the software program includes a formula $(CD_t - CD_{eq}) = (CD_0 - CD_{eq})e^{-(t/\tau)}$, where $CD_t$ is a concentration of the substance in the dialysis fluid at time t, $CD_{eq}$ is an equilibrium concentration of the substance in the dialysis fluid and is approximately equal to an equilibrium concentration of the substance in the patient's blood, $CD_0$ is an initial concentration of the substance in the dialysis fluid, t is time and $\tau$ is an equilibration time constant of a transport property of a peritoneum of the patient for the substance. In this embodiment, the software program is programmed to use the formula to calculate the equilibrium concentration of the substance and the equilibration time constant of the substance using the inputs and to suggest whether the peritoneum of the patient has a membrane transporter property selected from the group consisting of: a high transporter property, a high-average transporter property, a low-average transporter property, and a low transporter property.

A further embodiment of the present disclosure is a method for performing a simplified peritoneal equilibration test. The method includes steps of taking at least two samples of dialysis fluid after a start of a dialysis therapy, the samples taken at least two separate times, and analyzing the dialysis fluid samples only for concentrations of a substance in the dialysis fluid. The method also includes a step of calculating a $CD_{eq}$ using a formula $(CD_t-CD_{eq})=(CD_0-CD_{eq})e^{-(t/\tau)}$, where $CD_t$ is a concentration of the substance in the dialysis fluid at time t, $CD_{eq}$ is an equilibrium concentration of the substance in the dialysis fluid and is approximately equal to an equilibrium concentration of the substance in the patient's blood, $CD_0$ is an initial concentration of the substance in the dialysis fluid, t is time and τ is an equilibration time constant for a transport property of a peritoneum of the patient for the substance. In another embodiment, a method also includes a step of selecting a category of a membrane transporter property from among the known categories.

Still another embodiment of the present disclosure is a method for performing a simplified peritoneal equilibration test. The method includes steps of administering a peritoneal dialysis therapy to a patient, including taking at least two samples of dialysis fluid after a start of the dialysis therapy, the samples taken at times separated by at least about an hour. The method also includes steps of analyzing the dialysis fluid samples only for a concentration of creatinine, urea or glucose in the dialysis fluid samples, and then calculating a $CD_{eq}$ using a digital computer and a formula $(CD_t-CD_{eq})=(CD_0-CD_{eq})e^{-(t/\tau)}$, where $CD_t$ is a concentration of a substance in the dialysis fluid at time t, $CD_{eq}$ is an equilibrium concentration of the substance in the dialysis fluid and is approximately equal to an equilibrium concentration of the substance in the patient's blood, $CD_0$ is an initial concentration of the substance in the dialysis fluid, t is time and τ is an equilibration time constant for a transport property of a peritoneum of the patient for the substance. The method also includes a step of selecting a category of a membrane transporter property.

Embodiments of the present disclosure have an advantage in that a reasonable approximation of a patient's membrane transport properties is available with as few as two or three samples of dialysate fluid. Another advantage is that it is possible to classify the patient's membrane transport properties with this more convenient test. Another advantage is that a blood sample, and subsequent analysis of the blood sample, is not required. Thus, it is possible to carry out the S-PET at home or other location where it is not convenient to obtain a blood sample or to obtain an analysis of the blood sample.

Additional features and advantages are described herein, and will be apparent from the following Detailed Description and the figures.

DETAILED DESCRIPTION

Peritoneal equilibration tests date back to the work of Zyblut Twardowski et al. in *Peritoneal Equilibration Test, Perit. Dial Bull,* 7 (3), pp. 138-47 (1987) (hereinafter "Zyblut 1987"). and *Clinical Value of Standardized Equilibration Tests in CAPD Patients. Blood Purif,* 7, pp. 95-108 (1989). This work, and much work that followed, may be generally summarized with FIG. 1, which graphs on the abscissa or x-axis the ratio of $D/D_0$, the ratio of a concentration of glucose in the used dialysis fluid to the initial concentration of that same substance in the fresh dialysis fluid. The graph also presents on the ordinate or y-axis the ratio of the concentration of creatinine in the used dialysate to the concentration of creatinine in blood plasma, the ratio D/P, that is, in the concentration in the spent dialysis fluid to the concentration in the patient's blood plasma.

Figure 1:
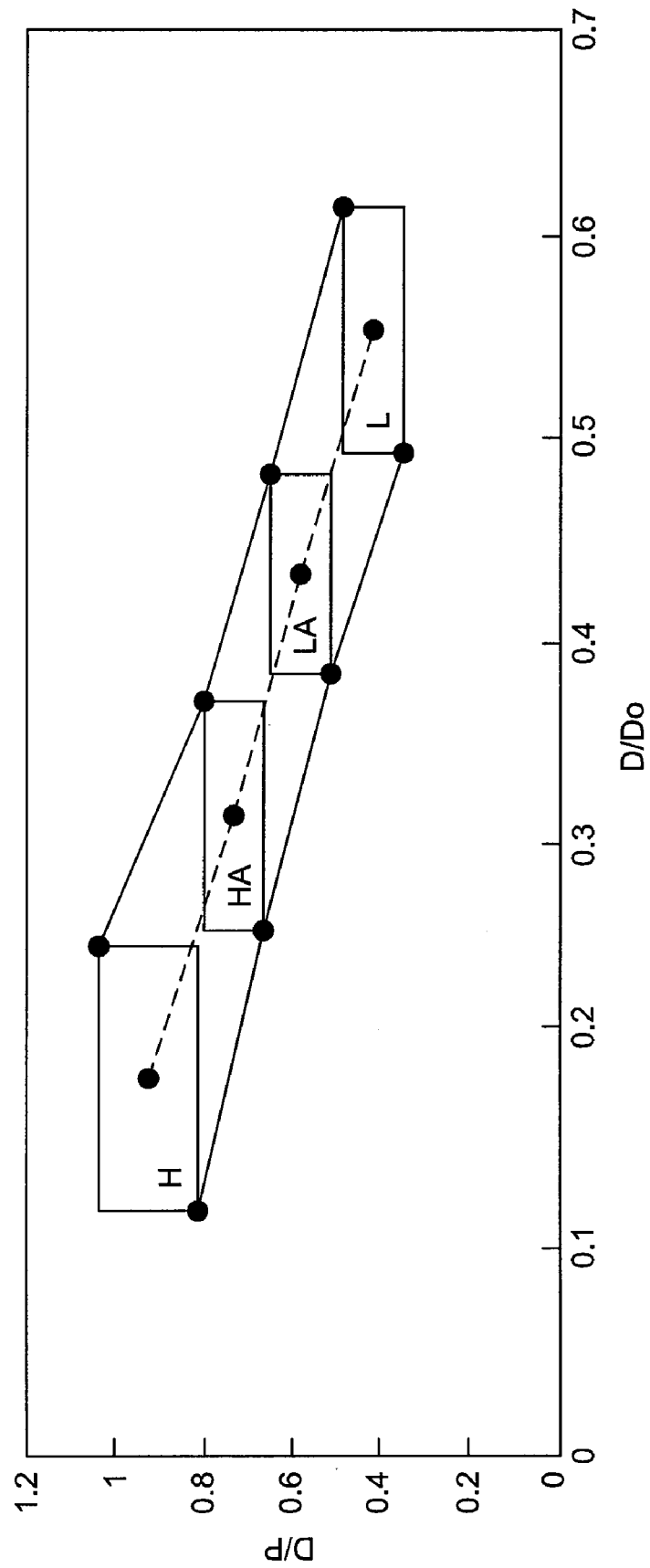
FIG. 1 is a prior art depiction of patient membrane categories.

Dialysis patients, or indeed the general population, may be classified by the transport characteristics of their peritoneal membrane into one of four categories, as shown in FIG. 1. "High" or "H" transporters have a higher ratio of a concentration of the waste-product solute in the dialysate fluid to that in their blood, and a lower ratio of glucose in the dialysis fluid to the initial concentration of glucose in the dialysis fluid, when compared to "low" or "L" transporters. Patients with intermediate transport characteristics may be classified as "high-average" or "HA" transporters, or "low-average" or "LA" transporters. In simpler terms, high transporters move the solutes through their peritoneum faster and achieve a higher D/P ratio, but glucose in the dialysate fluid also transports rapidly, and thus there is a lower ratio of solute to initial solute ($D/D_0$) in the spent dialysis fluid. Low transporters move the solutes through their peritoneum more slowly, but achieve higher ratios of solute in the spent dialysis fluid. High-average and low-average transporters are intermediate between these two.

In prescribing a therapy for high transporters, it is clear that a therapy should involve greater amounts of dialysis fluid and shorter dwell times for higher ultrafiltrate. For low transporters, lesser amounts of dialysis fluid may be combined with longer dwell times to achieve both higher ultrafiltrate and more solute removal.

FIG. 1 is a summary chart that leaves off much of the details in how these charts were prepared. As is well known to those with ordinary skill in the art, these charts are actually first constructed as time-scales, with time plotted on the abscissa and $D/D_0$ or D/P plotted on the ordinate. See Zyblut 1987. The ratio of $D/D_0$ and D/P may then be plotted, leaving out the time element. The result is an elegant solution that appears to neatly categorize patients.

In practice, a standard PET test may involve an entire eight to twelve hour night exchange with 3.86% or 2.27% glucose solution preceding the test exchange, if the test includes a kinetic analysis of the patient, which is not strictly necessary to determine the patient's membrane transport category. One technique is to then drain the abdomen completely over a twenty-minute period, and then infuse about two liters of 2.27% glucose over a ten-minute period. To obtain the initial sample, the patient is turned side to side and 200 ml is drained immediately after infusion, including a ten-ml sample for glucose, urea and creatinine. The remaining 190 ml is then returned for the dwell and this sampling procedure is repeated at several intervals, such as 30 minutes, one hour, two hours and three hours, each with a drain and a subsequent two-liter infusion. After the two hour sample is taken, a blood sample is also taken for tests for blood urea nitrogen ("BUN") and creatinine. A final infusion and dwell is taken at the four-hour mark, followed by a drain and a measurement of total effluent volume. There are many possible variations of the times at which samples are taken in a standard PET.

Once the above measurements are taken, the $D/D_0$ glucose and D/P creatinine results are used in a chart similar to those described above to classify the patient's peritoneal membrane in one of the four categories. This procedure is labor-intensive and very intrusive on the patient because of the number of samples needed, including a blood sample.

Since 1989, many attempts have been made to devise faster PET tests, but the method described above is still widely accepted and applied to assess peritoneal membrane function for peritoneal dialysis patients. Adcock et al. suggested a faster method in which the initial glucose concentration and other intermediate samples were not measured, and used only the plasma sample and the last, four-hour time point. Adcock et al., *Clinical Experience and Comparative Analysis of the Standard and Fast Peritoneal Equilibration Tests (PET), Advances in Peritoneal Dialysis*, vol. 8, pp. 59-61 (1992). La Milia suggested a method in which the standard four-hour dwell is replaced with a one hour dwell using a 3.86% glucose solution, but still required the blood sample. La Milia et al., *Mini Peritoneal Equilibration Test: A simple and fast method to assess free water and small solute transport across the peritoneal membrane, Kidney Int'l* 68, pp. 840-846 (2005).

Figure 2:
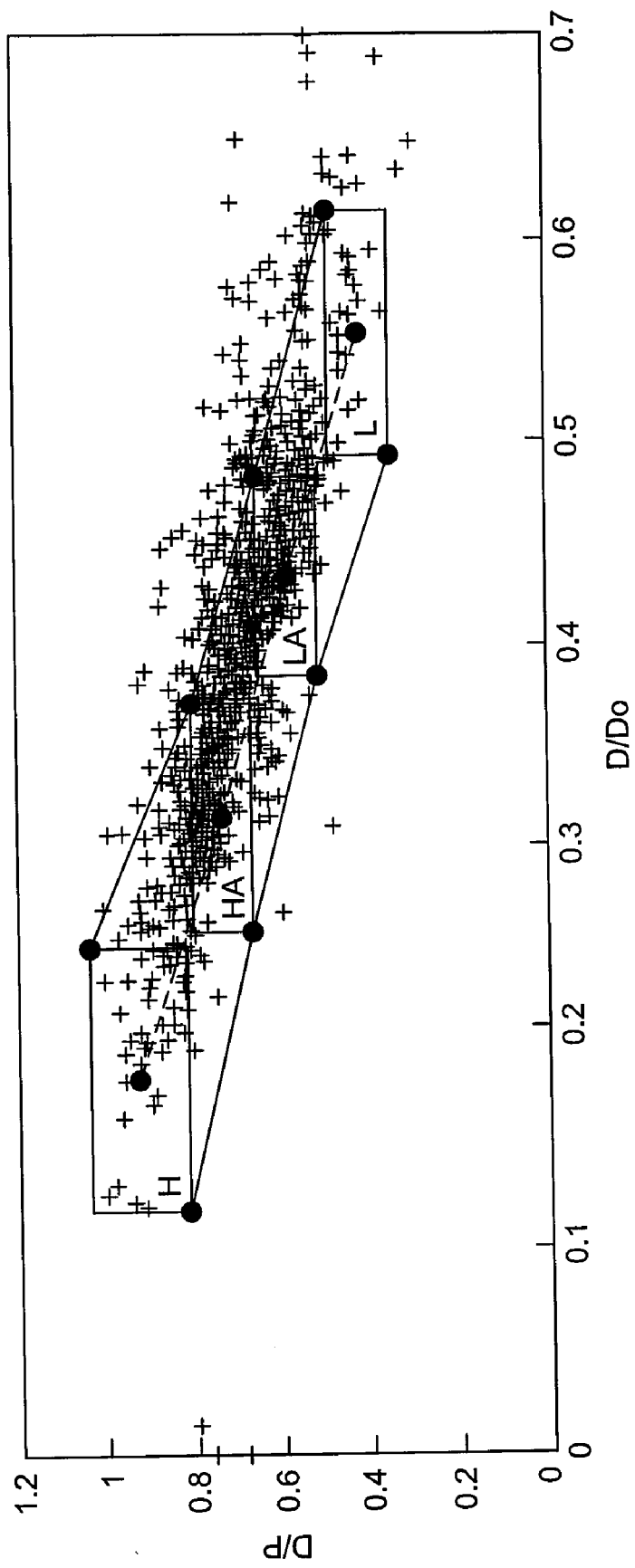
FIG. 2 is a graph of how the prior art fails to adequately place patients among the categories

The reality of classification schemes, however, is better depicted in FIG. 2. In studying about one-thousand patients for whom clinical data are available, it has been unexpectedly discovered that the above tests and the accepted categories do not correctly categorize about 40% of patients. FIG. 2 depicts the results of the survey for both the D/P and the $D/D_0$ axes. These data depict results using a standard PET as described above. Approximately 40% of the patients thus do not fit into any of the four categories. Another way of saying this is that the long and involved PET procedure described above does not correctly classify about half of all patients. It is expected that the shorter PETs discussed above will also misclassify or fail to classify at least about that percentage of patients.

Improved Procedure for the S-PET

The present disclosure describes a new test, the S-PET, that is less labor intensive and uses what may be described as more effective sampling. A peritoneal dialysis machine, such as a HomeChoice® dialysis machine, is helpful in administering the test. In this test, samples of the dialysis fluid are taken for analysis of urea, creatinine and glucose content. No blood sample is taken and either 2.27% glucose (Dianeal™ 2.27%) or 3.86% glucose (Dianeal™ 3.86%) dialysis solution may be used. Measurements may be taken initially, at thirty minutes and at the one, two and four hour marks. Based on these tests, an estimate for a curve-fit is made for a final creatinine concentration in the dialysis fluid. Tests may instead be based on only two or three readings, such as readings at four hours and eight hours, for example, or tests taken at one hour, two hours and eight hours. The reading at the start of the test may be taken as zero, for example, to spare the patient the discomfort and labor in taking what is likely the least-useful test. Alternatively, other time points may be used.

FIGS. 3A to 3D depict graphically the result of tests for creatinine for the four categories of patients, including a blood sample. Each of the graphs displays creatinine concentration test results plotted against the time period after infusion of the dialysis fluid. Each graph also marks a plasma creatinine concentration taken at about two hours. The final point in each graph is an estimate of the equilibrium creatinine concentration for the patient using a standard curve-fitting program, such as Excel™ from Microsoft Corp., Redmond, Wash., U.S.A. or MatLab™ from The MathWorks Inc., Natick, Mass., U.S.A.

Figure 3A:
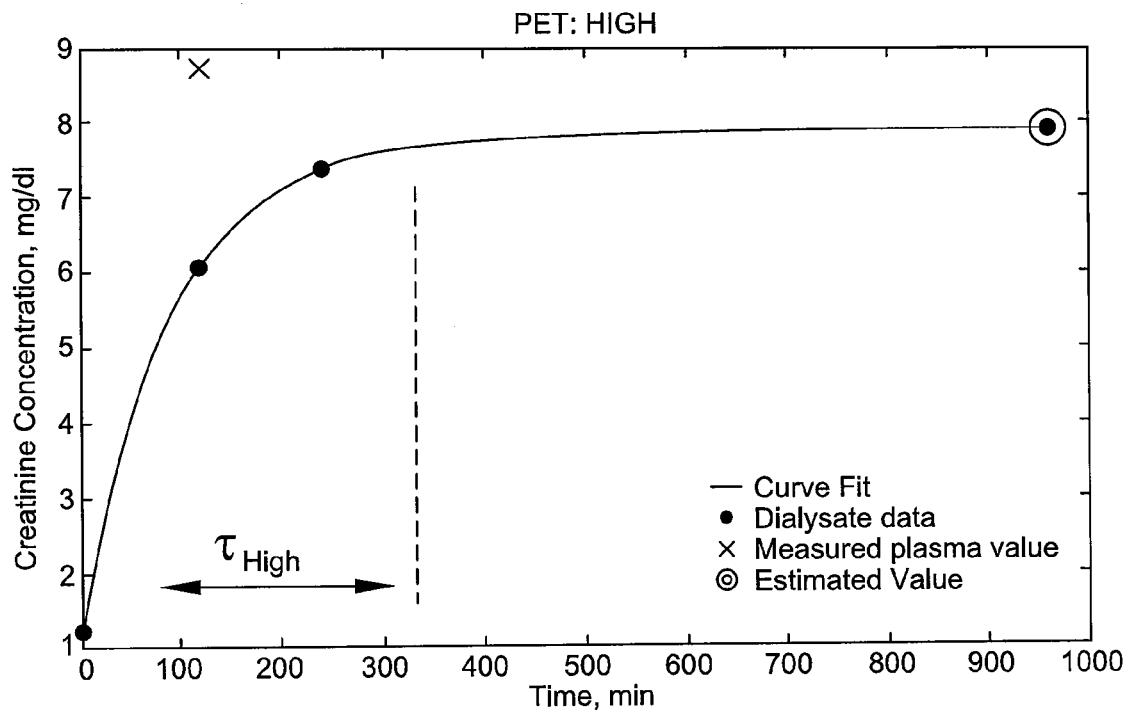
FIGS. 3A to 3D are charts depicting how the simplified PET test uses data points to categorize patients among the categories.

In FIG. 3A, the dialysis fluid for a typical high transporter patient is seen to have a rapidly-growing concentration of creatinine. In this category of patients, the creatinine concentration reaches a maximum after about 4 to 5 hours. There is thus no benefit in creatinine removal after a dwell period of about 4 to 5 hours. The test result is achieved simply by infusing the patient and then removing a 10 ml sample at the intervals for which the dots are shown, at the test beginning and after 2 hours and 4 hours. A curve fit is then used to estimate a final or equilibrium concentration for the solute that would be achieved in a very long dwell time. A computer is useful in finding a curve fit for the data. As seen in FIG. 3A, the curve fit is excellent and a final estimate of about 8 mg/dL is very close to the four-hour measurement of about 7.5 mg/dL.

At the time these tests were conducted, a blood plasma sample was also taken at about the 2-hour mark for confirmation. The blood plasma sample for the high-transporter patient had a plasma creatinine concentration of about 8.5 mg/dL at the 2-hour point. The plasma concentration samples taken and displayed at FIGS. 3A to 3D confirm that the plasma concentration is inversely related to membrane transport speed, as expected. That is, as creatinine clearance decreases, more creatinine remains in the patient's blood plasma.

Figure 3B:
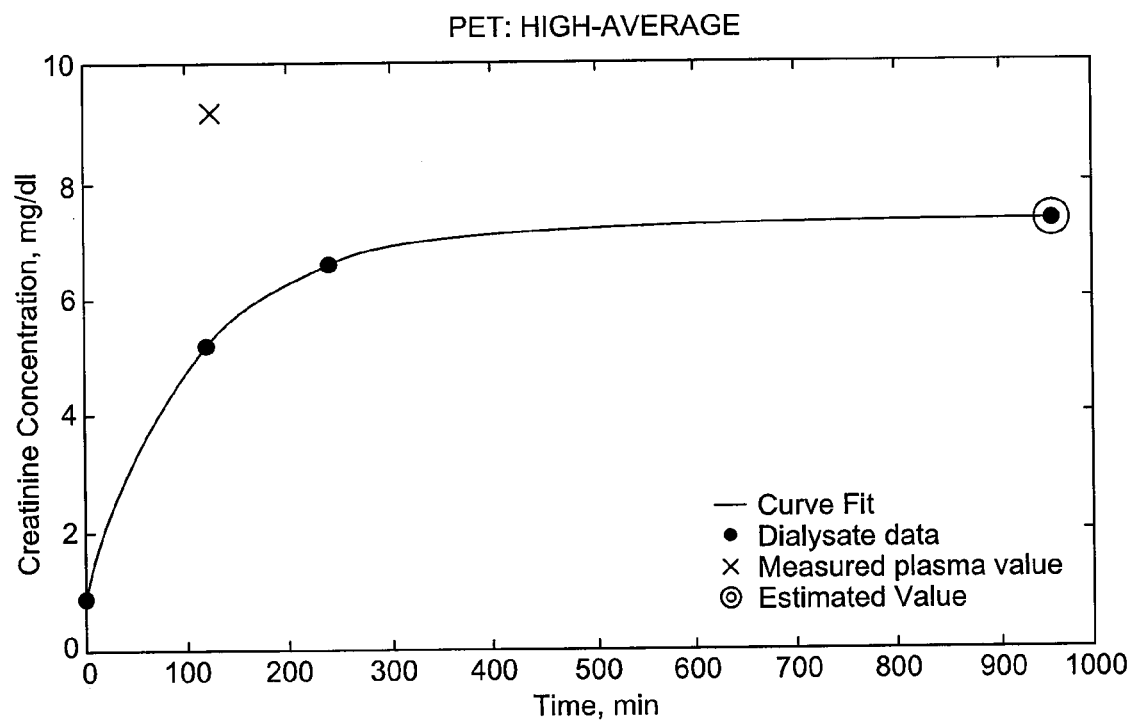

A similar result is seen in FIG. 3B, for patients who may be categorized as high-average transporters, that is, patients whose peritoneal membranes are somewhat less permeable than those of the high transporters. For these patients, the equilibrium concentration of creatinine is estimated at the end of the curve in FIG. 3B at about 7 mg/dL, which is very close to the 4-hour sample concentration of about 6.5 mg/dL. A blood plasma sample showed a creatinine concentration of about 9 mg/dL, a little higher than the high transporter patients, indicating that less creatinine was removed from these patients than from the high transporter patients.

Figure 3C:
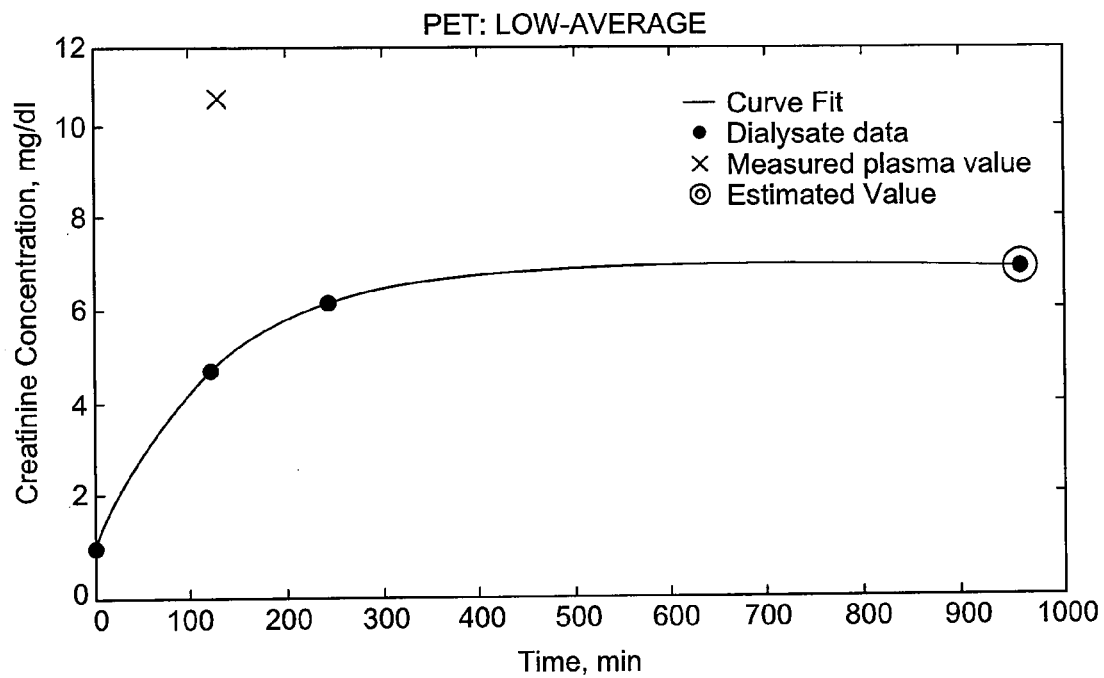

FIG. 3C depicts results for patients with peritoneal membranes that may be categorized as low-average transporters. Creatinine concentration in the 4-hour sample was about 6 mg/dL, a little lower than that shown for the high-average transporters. However, the estimate for the equilibrium creatinine concentration was about 7 mg/dL, very close to that for the high-average transporters. The blood plasma sample shows significantly more creatinine, about 11 mg/dL, compared to high and high-average transporters.

Figure 3D:
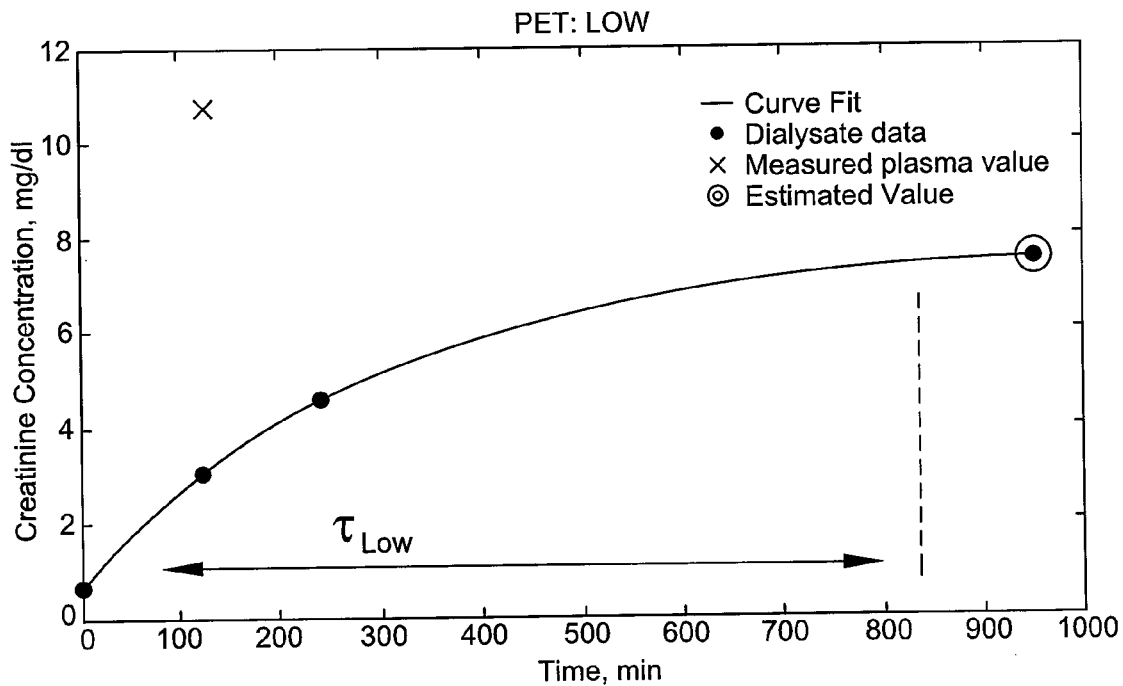

FIG. 3D depicts results for low-transporter patients, that is, those patients whose peritoneal membranes are least amenable to mass transfer. As FIG. 3D depicts, there is no rapid rise in creatinine concentration in the first four hours, compared with the other three categories of transporters. However, the concentration continues to rise over a longer period of time, with an eventual final estimate for the equilibrium concentration of about 7.5 mg/dL, which is close to low-average and high-average transporters. The blood plasma creatinine level at the two-hour mark was about 11 mg/dL, similar to low-average transporters, and significantly higher than patients with membranes classed as either high or high-average. Thus, patients with peritoneal membranes classed as high or high-average are seen to have lower creatinine levels after two hours of dialysis than patients with low or low-average peritoneal membranes.

FIGS. 3A to 3D depict the rise of creatinine levels in spent dialysis fluid. If urea were used as the solute of interest, a similar series of curves would result, but with less noticeable differences between the curves because of the faster transport of the small urea molecules across the peritoneal membrane. Of course, glucose in the dialysis fluid would be expected to decrease, as the glucose is transported from the dialysis fluid across the peritoneal membrane and infuses into the blood of the patient. High transporters would be expected to see a rapid infusion of glucose, while low transporters would expect a slower infusion. Since glucose is the osmotic agent in the dialysis fluid, the loss of glucose from the dialysis fluid lowers its effectiveness in providing the driving force for ultrafiltration.

While conducting this work, it was discovered that the data depicted in FIGS. 3A to 3D may be fit to a curve using the following equation:

$$(CD_t - CD_{eq}) = (CD_0 - CD_{eq})e^{-(t/\tau)},$$

where $CD_t$ is a concentration of the at least one substance at one of the separate times at which dialysis fluid samples are taken, $CD_{eq}$ is an equilibrium concentration of the at least one substance, $CD_0$ is an initial concentration of the at least one substance, t is one of the separate times and $\tau$ is an equilibration time constant that is representative of a transport property of a peritoneum of the patient. $CD_{eq}$ and $\tau$ may be estimated using this equation and a curve fit program, based on the measured solute concentrations in the samples taken. $CD_{eq}$ is an equilibrium concentration of the substance in the dialysis fluid and is approximately equal to a concentration of the substance in the patient's blood at equilibrium, that is, after a long period of time.

In the limited numbers of patients used in this work, the equilibration time constant for the four categories of transporters were found to be, respectively, 107 minutes, 175 minutes, 242 minutes and 406 minutes, for creatinine for high, high-average, low-average and low transporters, respectively. To determine a final set of numbers, clinical studies with large number of patients should be conducted. Time constants for glucose and urea are expected to be different. In one embodiment, the formula is made part of a computer software program, which is entered into a computer memory or placed onto a medium accessible to a computer for performing calculations necessary to derive the $CD_{eq}$ of the substance for the particular patient.

The test results may be analyzed and graphed in a variety of ways to increase their utility and also to increase the confidence that the new labor-saving test procedure can be used rather than the more arduous traditional PET. For urea and creatinine, the ability to predict the equilibrium levels in the dialysis fluid means that the equivalent levels of plasma urea and creatinine are not needed. These correlations may be used with confidence and the labor saved makes the procedure easier for both patients and caregivers. Additional data points may be used in the above formula if the information is available from additional samples of dialysate from the patient.

One advantage of this procedure is that it may be used in a variety of circumstances where an easier procedure to obtain the results is important. While a blood sample, as seen, is useful, it is not strictly necessary for obtaining results similar to those seen in FIGS. 3A to 3D. Thus, the test may be performed at a hospital, an out-patient clinic, or even at home. This may be useful, for example, as an update if a patient or a caregiver has reason to suspect that the transport properties of the membrane of the patient have changed.

With updated test results, the patient or a caregiver may alert a physician to the change and suggest that a change in prescription may be appropriate. The physician or caregiver may use the test results to compare to previous test results, if any, and see whether there has indeed been a change in test results for the patient of interest. These test results may be used in conjunction with suitable software, such as PDAdequest® or RenalSoft™ from Baxter International Inc., Deerfield, Ill., USA. This software may then be used by the physician to update a prescription for the patient.

The samples from the dialysis fluid may be analyzed by standard laboratory instruments at a clinic or hospital. To analyze the samples at home, it is useful to have home kits with tools or instruments for analyzing the samples. Kits for analyzing the test results may include smaller, substance-specific instruments, test strips, cuvettes for dialysis fluid samples for insertion into the instruments, suitable pumps, and so on. Some specific procedures are described below.

Analyses for the S-PET

The test may be performed and samples taken using a standard peritoneal dialysis machine, such as the Baxter HomeChoice® peritoneal dialysis machine. The machine is programmed to take samples at the appropriate times, such as at the start of dialysis and at two hours and four hours. In another example, samples may be taken at two hours and eight hours, or at four hours and eight hours. The samples are then analyzed for the appropriate solute or solutes, such as glucose, urea or creatinine. For patients using automated peritoneal dialysis ("APD"), the machine is programmed as desired and the patient may already be equipped with a kit or a disposable that includes the necessary tools to detect or measure the appropriate solute. These tools may include chemical reagents, test strips, optical components, conductivity cells, pH cells, and the like.

For example, a microfluidic chemical analyzer system can be used to detect the concentration of the substance, i.e. creatinine, urea, and glucose, in the dialysate. The microfluidic system may consist of small-scale channels, pumps, and detection systems. Microfluidic channels may be chemically treated to alter material surface properties in order to achieve preferred surface tension characteristics to induce motion of the dialysate, i.e. passive pumping. Alternatively, an active micro pump can be used to move the dialysate within the microfluidic analyzer. Using this motion, micro-volume dialysate samples can be obtained and routed to the detector for the appropriate analysis. The same technique, or a variety of techniques, i.e. chemical, reagent, optical, or other technique, may be used to detect the level of desired substance concentration. The microfluidic analyzer may or may not be a part of the disposable set used by the patient for the dialysis therapy. Microfluidic disposable systems are available from, for example, Weidmann Plastics Technology, AG, Rapperswil-Jona, Switzerland, and ThinXXS Microtechnology AG, of Zweibrucken, Germany.

In another example, test strips and a readout may be used for glucose and creatinine. Such systems are available from Polymer Systems Technology, Inc., Indianapolis, Ind., USA, under the trade name of CardioChek and Bioscanner Creatinine Test Strips. Test strips are described, for example in U.S. Pat. No. 6,130,054 and U.S. Pat. Appl. Publ. 2006/0228767, both of which are hereby incorporated by reference in their entirety. Test strips for urine are also described, for example, in U.S. Pat. No. 6,699,720. Such analytical strips, and others, are typically impregnated with one or more reagents for reaction with the analyte or solute of interest. The reaction then results in a color change or an appearance change indicative of a concentration of the analyte of interest. In addition to strips of paper or plastic, such as strips about 3 to 5 mm wide, 5 to 10 cm long, these disposable, one-time-use devices may take the form of small containers or cuvettes. The container or cuvette may be impregnated or coated on its inside with reagents for detecting the solute or analyte of interest. After a dialysis fluid sample is obtained, the sample is pumped or drained into the container. The container may allow for a short residence time, if needed, and then the concentration is indicated by a color change, by the appearance of one or more lines, or other appearance change.

Optical methods are well known and are especially useful for testing for concentrations of urea. Such assay kits are available, for example, from BioAssay Systems, Hayward, Calif., USA. Other methods well known to those with skill in analytical art include conductivity probes, pH meters, and so forth. There are many ways to detect the solute or solutes of interest once the samples have been obtained at the prescribed or appropriate time intervals. Whether disposable or reusable, these techniques will work well at home or in environments where a sophisticated medical or chemical laboratory is not available.

In one embodiment, a home device or a kit may include test strips, reagents, or measuring devices designed to capture samples of the dialysis fluid for analysis of one or more of the primary solutes of interest, e.g., creatinine, urea or glucose. Thus, as noted, for a patient using APD, the dialysis machine may include a disposable accessory or a kit for capturing samples and measuring the solute of interest by one of the means discussed above. For patients using CAPD, there is no machine that provides constant service, and a home kit for administering a simplified peritoneal equilibration test (S-PET) may include the necessary reagents, devices, or strips for analysis. A pump for appropriate sampling of dialysis fluid may be obtained, for example, from ThinXXS Microtechnology AG, of Zweibrucken, Germany. The Bimor pump is available from Nitto-Kohki Inc., of Tokyo, Japan. An electro-kinetic pump is also available from Eksigent Technologies, Inc, of Dublin, Calif., USA.

Figure 4:
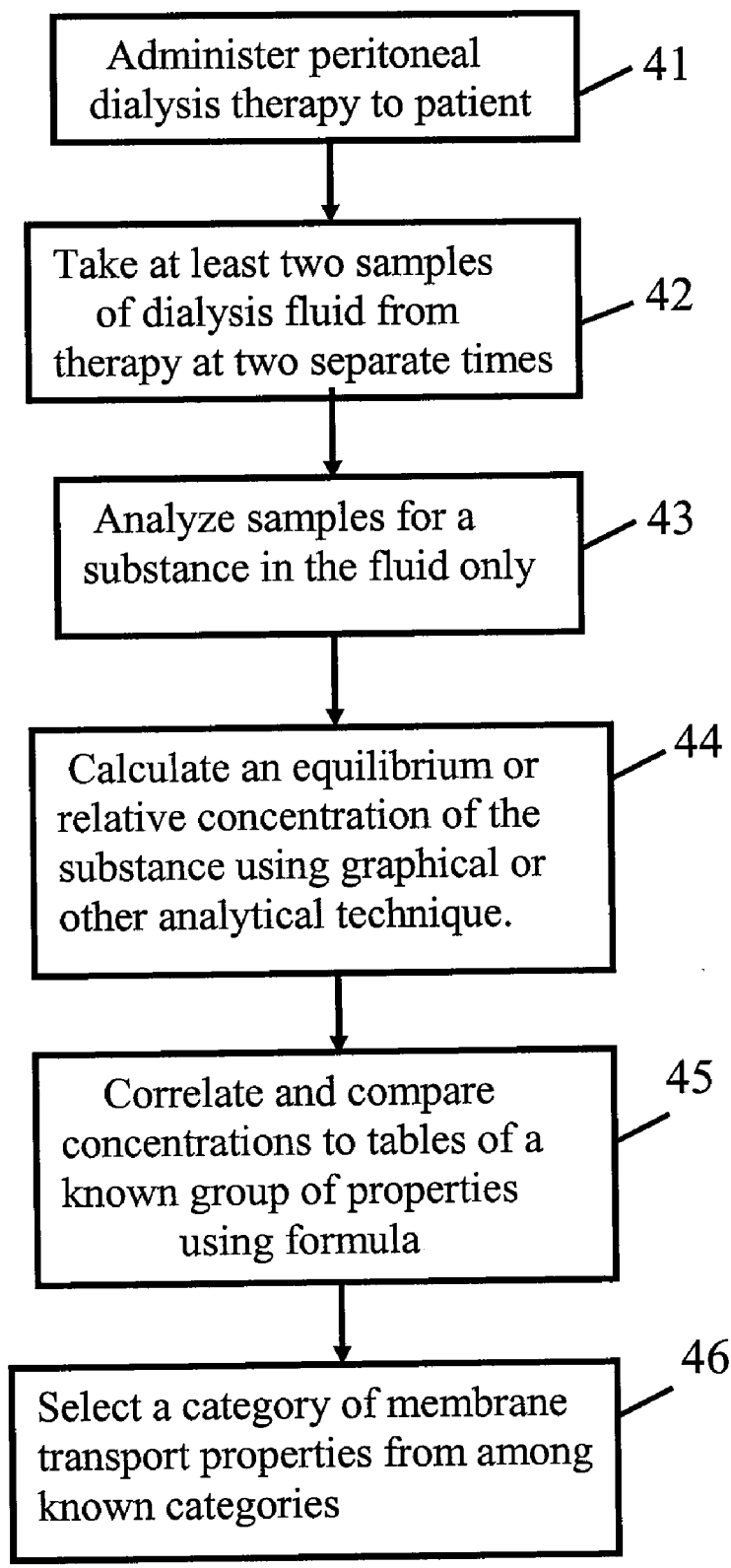
FIG. 4 is a flow chart depicting the classifying method disclosed herein.

The improved test also may include a measure of ultrafiltrate ("UF"), that is, the amount of water crossing the peritoneal membrane and causing an increase in the volume that is ultimately drained from the patient during dialysis. The amount of UF generated is an important determinant of patient transport status. The amount of UF generated can be measured with standard APD machines, such as the balance chambers in a HomeChoice™ peritoneal dialysis machine. An integrated scale may be used instead. For CAPD patients, a scale or flow measurement device may be used. Any of these measurements may be used in the S-PET to help determine the transport category of a patient, understanding that patients with high or high-average transporting membranes will tend to generate ultrafiltrate more quickly than patients with low or low-average transporting membranes The methods described above may be summarized in the flow-chart of FIG. 4 or other embodiments. The method of FIG. 4 is used to administer an S-PET to a patient as part of a process for administering peritoneal dialysis therapy. The test involves administering 41 peritoneal dialysis therapy to the patient and also taking 42 at least two samples of dialysis fluid from the dialysis therapy at two separate times. As discussed above, the times may include an initial sample at the beginning of the therapy, followed by additional samples 2 hours and 4 hours later. Alternatively, a zero concentration may be assumed for the initial sample and two samples may be taken at later times. The samples are analyzed for concentrations of an analyte of interest, such as urea, creatinine or glucose. The analysis is typically conducted via a chemical, optical, calorimetric, or other accepted analytical technique. Of course, more samples may be taken, and the longer the dwell time, typically, the better, because the sample gets closer to its actual equilibrium value, $D_{eq}$, for the solute of interest.

In one embodiment, two such samples may be taken and analyzed 43 for their creatinine concentrations. The formula may also be used to calculate the time constant for the appropriate substance, which may be accomplished at the same time or independently. Note that the equation has two unknowns, the $D_{eq}$ and the time constant. These concentrations may then be used to calculate 44 the equilibration concentration, $D_{eq}$, of creatinine, per FIGS. 3A to 3D, using the equation and time constants given above. Other analytical calculating techniques may be used, such as comparing the samples with previously-compiled tables or graphs of concentrations of the substance for known transporter types over periods of time. One of these analytical techniques is then used to correlate 45 the results of the analysis to known transporter properties. A selection is then made 46 of which transport category most closely matches the test results for the patient.

Of course, if a level of creatinine in the blood plasma (P) is known or may be estimated for a patient, the level of creatinine at the four hour mark, $D_4$, or other time, may then be used to calculate D/P, such as $D_4/P$, the relative concentration of creatinine at four hours to blood level at the appropriate time. A table may then be used to compare $D_4/P$ to known categories of transport groups, and the appropriate categorization or selection may then be made. These tables, as well as others, may also be entered into a computer memory so that the necessary calculations may be accomplished with a computer. The computer may be the same computer used to operate a peritoneal dialysis machine, or may be a different computer. In general, it may not be strictly necessary to determine a patient's classification in order to prescribe an appropriate therapy. Data from a patient may be used with graphs such as those depicted in FIG. 2 to determine the appropriate therapy without necessarily determining a specific transporter category.

In another embodiment, and with respect to FIG. 4, two or more samples may be taken and analyzed 43 for their glucose concentrations. The concentration of glucose at the four hour mark may be divided by the initial concentration of glucose, i.e., the value of $D_4/D_0$ determined 44, thus performing a mathematical operation to determine a concentration of the glucose at the four hour mark relative to the concentration of glucose at the start of the therapy. The result may then be compared 45 to tables of a known group of properties using a graph such as FIG. 4. The appropriate category of membrane transport properties may then be selected 46 from among the accepted or known categories by using a graph or by using software. It is also possible to simply use the test results as inputs to a peritoneal dialysis software program, such as PD Adequest™ or RenalSoft™, from Baxter International, Inc.

Additional calculations and refinements may be made during the process as additional information becomes available. For example, measurements may be made using solute levels at three different times, such as at the start of the test, and at two and four hours, and the equilibration time constant used with the equation above to estimate an initial fit and category selection. A fourth data point may then be estimated, and using the four data points, a second iteration run to refine the data and achieve a better approximation.

Additional considerations may be needed for some groups of patients. For instance, the glucose levels may require special attention when dealing with diabetic patients. Glucose levels in diabetic patients may not be constant and thus the transport of glucose from dialysis fluid may be highly variable depending on whether glucose levels in the patient's blood are in control, or are instead elevated or depressed out of normal ranges, e.g., 70-99 mg/dL. Instead of relying only on glucose levels, it may be prudent to use creatinine or urea instead of or in addition to glucose levels. Other waste products of interest may also be used.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A system for performing a simplified peritoneal equilibration test, the system comprising:
 a computer; and
 a non-transitory computer-readable medium accessible to the computer and containing a software program therein, wherein the software program is programmed to cause a computer processor to accept inputs concerning at least two concentrations of a substance in samples of a dialysis fluid from at least two separate times after a start of a dialysis therapy of a patient, wherein the software program includes a formula $$(CD_t - CD_{eq}) = (CD_0 - CD_{eq})e^{-(t/\tau)},$$

where $CD_t$ is a concentration of the substance in the dialysis fluid at time t, $CD_{eq}$ is an equilibrium concentration of the substance, $CD_0$ is an initial concentration of the substance in the dialysis fluid, t is the time and $\tau$ is an equilibration time constant of a transport property of a peritoneum of the patient for the substance,
 wherein the software program is programmed to cause the computer processor to use the formula to calculate the $CD_{eq}$ of the substance wherein the $CD_{eq}$ is approximately equal to an equilibrium concentration of the substance in the blood of the patient, and wherein the software program is further programmed to cause the computer processor to suggest at least one transport property of the peritoneum of the patient.

2. The system according to claim 1, wherein the at least two samples comprise a first sample from an overnight cycle and a second sample from a subsequent cycle.

3. The system according to claim 1, wherein the software program is configured to cause the computer processor to accept an additional input concerning a concentration of the substance in an additional sample of dialysate and to perform at least one additional calculation to confirm the suggestion of the transport properties.

4. The system according to claim 1, further comprising a peritoneal dialysis machine, wherein the computer is configured for operating the peritoneal dialysis machine.

5. The system according to claim 1, further comprising a kit for analyzing for the substance in the samples of dialysis fluid, the kit comprising disposable strips or containers with indicators for the substance.

6. The system according to claim 5, wherein the kit further comprises a pump for pumping the dialysis fluid samples to a disposable or reusable container for analysis.

7. The system according to claim 1, wherein the software program is further programmed to cause the computer processor to suggest whether the peritoneum of the patient has a transport property selected from the group consisting of: a high transporter property, a high-average transporter property, a low-average transporter property, and a low transporter property.

8. A system for performing a simplified peritoneal equilibration test, the system comprising:
 a peritoneal dialysis machine;
 a computer for operating the peritoneal dialysis machine; and
 a non-transitory computer-readable medium accessible to the computer and containing a software program therein, wherein the software program is programmed to cause a computer processor to accept inputs concerning at least two concentrations of a substance in samples of a dialysis fluid from at least two separate times from a dialysis therapy of a patient, wherein the software program includes a formula $$(CD_t - CD_{eq}) = (CD_0 - CD_{eq})e^{-(t/\tau)},$$

where $CD_t$ is a concentration of the substance in the dialysis fluid at one of the separate times, $CD_{eq}$ is an equilibrium concentration of the substance and is approximately equal to an equilibrium concentration of the substance in the patient's blood, $CD_0$ is an initial concentration of the substance in the dialysis fluid, t is time and $\tau$ is an equilibration time constant of a transport property of a peritoneum of the patient for the substance,
 wherein the software program is programmed to cause the computer processor to use the formula to calculate the $CD_{eq}$ of the substance and the equilibration time constant of the substance using the inputs and to suggest whether the peritoneum of the patient has a membrane transport property selected from the group consisting of: a high transporter property, a high-average transporter property, a low-average transporter property, and a low transporter property.

9. The system according to claim 8, wherein the software program is operable to cause the computer processor to accept a desired outcome of a dialysis therapy and to calculate parameters of at least one dialysis therapy session.

10. The system according to claim 9, wherein the desired outcome is selected from the group consisting of a glucose absorption, a creatinine clearance, a urea clearance or an ultrafiltrate volume.

11. The system according to claim 9, wherein the calculated parameters comprise a glucose concentration, a dwell time, a therapy volume and a fill volume.

12. The system according to claim 8, further comprising a kit for analyzing for the substance in the at least two samples of dialysis fluid, the kit selected from the group consisting of a microfluidic kit, a kit with disposable strips and a kit with containers with indicators for the substance.

13. A method for performing a simplified peritoneal equilibration test, the method comprising:
 taking at least two samples of a dialysis fluid at least two separate times after a start of a dialysis therapy;
 analyzing the at least two dialysis fluid samples ofto obtain concentration data corresponding to a substance in the dialysis fluid; and
 calculating, using a digital computer and the concentration data, a $CD_{eq}$ using a formula $$(CD_t - CD_{eq}) = (CD_0 - CD_{eq})e^{-(t/\tau)},$$

where $CD_t$ is a concentration of the substance in the dialysis fluid at time t, $CD_{eq}$ is an equilibrium concentration of the substance in the dialysis fluid and is approximately equal to an equilibrium concentration of the substance in the patient's blood, $CD_0$ is an initial concentration of the substance in the dialysis fluid, t is time and τ is an equilibration time constant for a transport property of a peritoneum of the patient for the substance.

14. The method according to claim 13, further comprising selecting a category of a membrane transporter property from among the known categories.

15. The method of claim 14, wherein the category is selected from the group consisting of a high transport property, a high-average transporter property, a low-average transporter property, and a low transporter property.

16. The method of claim 13, wherein the substance is selected from the group consisting of creatinine, urea and glucose.

17. The method of claim 13, further comprising analyzing an additional dialysate sample of the patient for the substance and using a result of the analysis in the step of calculating.

18. The method of claim 13, wherein the formula is embedded on a non-transitory computer readable medium accessible to the digital computer.

19. The method of claim 13, wherein the at least two samples include a sample taken after about four hours or eight hours of dwell time.

20. The method of claim 13, wherein the step of analyzing is conducted using a microfluidic chemical analyzer.

21. The method of claim 13, wherein the step of analyzing is conducted using a reusable analytical system.

22. A method for performing a simplified peritoneal equilibration test, the method comprising:
   administering a peritoneal dialysis therapy to a patient;
   taking at least two samples of dialysis fluid after a start of the dialysis therapy, the samples taken at times separated by at least about an hour;
   analyzing the dialysis fluid samples to obtain concentration data corresponding to creatinine, urea or glucose in the at least two dialysis fluid samples;
   calculating, using the concentration data, a $CD_{eq}$ using a digital computer and a formula $$(CD_t - CD_{eq}) = (CD_0 - CD_{eq})e^{-(t/\tau)},$$

where $CD_t$ is a concentration of a substance in the dialysis fluid at time t, $CD_{eq}$ is an equilibrium concentration of the substance in the dialysis fluid and is approximately equal to an equilibrium concentration of the substance in the patient's blood, $CD_0$ is an initial concentration of the substance in the dialysis fluid, t is time and τ is an equilibration time constant for a transport property of a peritoneum of the patient for the substance; and
   selecting a category of a membrane transporter property.

23. The method of claim 22, further comprising programming a peritoneal dialysis machine for a peritoneal dialysis cycle after the step of selecting the category.

* * * * *